(12) United States Patent
Fetzner et al.

(10) Patent No.: US 10,095,839 B1
(45) Date of Patent: Oct. 9, 2018

(54) METHOD AND SYSTEM FOR MONITORING REMOTE SERVICES

(71) Applicant: At Homes FMS, LLC, Erie, PA (US)

(72) Inventors: James P. Fetzner, Erie, PA (US); Louis R. Rieger, Erie, PA (US)

(73) Assignee: FMS, LLC, Erie, PA (US)

( * ) Notice: Subject to any disclaimer, the term of this patent is extended or adjusted under 35 U.S.C. 154(b) by 847 days.

(21) Appl. No.: 13/667,340

(22) Filed: Nov. 2, 2012

Related U.S. Application Data

(60) Provisional application No. 61/671,317, filed on Jul. 13, 2012, provisional application No. 61/555,180, filed on Nov. 3, 2011.

(51) Int. Cl.
| | |
|---|---|
| *G06F 19/00* | (2018.01) |
| *G16H 10/60* | (2018.01) |
| *G16H 40/20* | (2018.01) |
| *G16H 50/20* | (2018.01) |

(52) U.S. Cl.
CPC ........ *G06F 19/3418* (2013.01); *G06F 19/328* (2013.01); *G16H 10/60* (2018.01); *G16H 40/20* (2018.01); *G16H 50/20* (2018.01)

(58) Field of Classification Search
CPC .. G06F 19/322; G06F 19/3456; G06F 19/327; G06F 19/3418; G06F 19/3443; G06F 19/3481; G06F 19/363; G06F 19/321; G06F 19/323; G06F 19/328; G06F 19/3431; G06F 19/366; G06F 21/6254; G06Q 50/22; G06Q 50/22; G06Q 50/24; G06Q 10/10; G06Q 30/04; G16H 10/60; G16H 40/20; G16H 50/20
USPC ........................................................ 705/2, 3
See application file for complete search history.

(56) References Cited

U.S. PATENT DOCUMENTS

| | | |
|---|---|---|
| 5,867,688 A | 2/1999 | Simmon et al. |
| 7,308,426 B1 | 12/2007 | Pitroda |
| 7,543,149 B2 | 6/2009 | Ricciardi et al. |
| 7,945,456 B2 | 5/2011 | Schoenberg |
| 2008/0059228 A1* | 3/2008 | Bossi et al. ............... 705/2 |
| 2011/0010087 A1* | 1/2011 | Wons ............... G06F 19/327 701/533 |
| 2011/0257994 A1 | 10/2011 | Givens et al. |
| 2013/0018688 A1* | 1/2013 | Nudd ............... G06Q 10/109 705/7.15 |
| 2014/0052466 A1* | 2/2014 | DeVille et al. ............... 705/2 |

* cited by examiner

*Primary Examiner* — Maroun P Kanaan
(74) *Attorney, Agent, or Firm* — Bodi Law LLC

(57) ABSTRACT

A method and apparatus (or a System) that facilitates the communication of health care or other information and tasks between and among clients (e.g., patients), providers/employees/suppliers (e.g., caregivers), State Agencies (or insurance providers), and other third party agencies. The providers can then be located in the client homes to provide health and/or medical or other services to the clients.

32 Claims, 15 Drawing Sheets

| Lou | | | |
|---|---|---|---|
| Arrival Time: | Departure Time: | Hours: | |
| Thu Feb 23 03:00 PM | Thu Feb 23 05:00 PM | 2h 00m | Luke |
| Wed Feb 22 03:15 PM | Wed Feb 22 07:15 PM | 4h 00m | Ty |
| Wed Feb 22 03:00 PM | Wed Feb 22 03:15 PM | 0h 15m | Ty |
| Wed Feb 22 10:00 AM | Wed Feb 22 10:00 PM | 12h 00m | Luke |
| Tue Feb 21 09:00 AM | Tue Feb 21 05:00 PM | 8h 00m | Ty |

You have approved 0 hours and 0 minutes this pay period, from Sun Feb 12 to Sat Feb 25

FIG. 5B

Mary Miller's Time

| Start Time | End Time | Hours | Select All |
|---|---|---|---|
| 6/13/2011 8:00am | 6/13/2011 4:30pm | 8.5 | |
| 6/14/2011 8:00am | 6/14/2011 9:00pm | 1.0 | |
| 6/15/2011 8:00am | 6/15/2011 4:30pm | 8.5 | |
| 6/16/2011 8:00am | 6/16/2011 12:00pm | 4.0 | |
| 6/17/2011 8:00am | 6/17/2011 4:30pm | 8.5 | |
| Approved Hours | | 30.5 | Remaining Authorized Hours: 2.5 |

*I understand that Medicaid fraud is a federal offence that may involve penalties and/or criminal prosecution.*

I Approve These Hours

*Home with Ease*℠

FIG. 6B

METHOD AND SYSTEM FOR MONITORING REMOTE SERVICES

CROSS-REFERENCES TO RELATED APPLICATIONS

This application claims the benefit of provisional application Ser. No. 61/555,180 filed on Nov. 3, 2011, incorporated herein by reference. This application also claims the benefit of provisional application Ser. No. 61/671,317 filed on Jul. 13, 2012, incorporated herein by reference.

BACKGROUND

Medical/health care providers ("care providers") are increasingly being put under pressure to improve their outcomes and decrease costs. Outpatient services are one way to decrease costs by not requiring patients to utilize hospitals. Whether patients are discharged from hospitals or outpatient services, means of reducing re-admissions are desirable to reduce costs, and in fact, government agencies and insurance companies are putting pressure on care providers to avoid costly re-admissions. Finally, patient home care is increasingly being utilized to avoid nursing home costs and risks (such as risk of transmitting communicable infections).

To support all of these services in a reduced-cost matter, such care providers are increasingly bringing services to the homes of the patients. Follow up care is utilized to help prevent costly readmissions, and to ensure that the patients are complying with doctor ordered drug and therapy regimes. Furthermore, nurses, skilled therapists, and other service providers are visiting the homes of the patients to provide such services. Such providers of services can often thereby visit the homes of patients to provide their services.

However, a problem exists that currently, it is difficult to ensure that these providers are performing the services for which they are being paid. Visits are typically self-reported by the provider employee, and thus can easily be improperly reported or even fraudulently misrepresented. Currently, provider activities done in patient homes use paper systems utilizing a "time sheet" that is filled out manually by the provider employee and then signed by both the Provider employee and the patient (client) and then forwarded to a third party for processing. However, such time sheets are basically validated by an "honor system" that accepts the word of the provider employee and client. The client does not typically work as an effective check or verification on this process, as there is rarely much motivation on the client to check the actual time entries of the provider employee, because the client is typically not paying directly for the services and in some cases may not be mentally capable of checking the employee's entries.

Hence, payer organizations desire proof and more effective verifications that such provider employees are actually providing the services for which the provider is billing the payer. Hence, a means of better ensuring that the services being billed have actually been performed is desirable.

SUMMARY

Provided are a plurality of example embodiments, including, but not limited to, a method for verifying provider services provided by a provider to a client in the client's home, the method comprising the steps of:

providing a first user interface on a remote computerized terminal adapted for accepting time information from the provider providing health services to the client at the client's home;

providing a second user interface on the computerized terminal for accepting validation information from the client for approving the time information accepted from the provider;

the computerized terminal collecting verification information for verifying that the time information accepted from the provider was entered with the terminal located at the client's home;

using the verification information for verifying that the time information accepted from the provider was entered with the terminal at the client's home;

subsequent to a successful verifying, using a computer server remotely connected to the terminal via a communication network for formatting an electronic bill according to a predetermined format acceptable to a payment agency separate from the provider; and the computer server electronically sending the bill to the payment agency for use by the payment agency for paying the provider for the provider services.

Also provided is a method for verifying provider services provided by a provider to a client in the client's home, the method comprising the steps of:

providing a remote computerized terminal located in the client's home;

providing an enrollment interface for enrolling the provider using the remote computerized terminal, wherein the enrolling step includes the step of the client engaging the services of the provider for providing the health services to the client in the client's home, the engagement step including the step of collecting information from the client regarding the health services to be performed;

using the remote computerized terminal for verifying that the client engaged the services of the provider for providing the health services; and using the remote computerized terminal when the provider is providing the health services to the client.

Still further provided is a method for verifying provider services provided by a provider to a client in the client's home, the method comprising the steps of:

providing a remote computerized terminal located in the client's home;

providing a provider interface on the remote computerized terminal for accepting information from the provider, wherein the information is formatted for use in support of providing the health services to the client;

providing a client interface on the remote computerized terminal for accepting verification information from the client for use in verifying the providing of the health services to the client; and using the remote computerized terminal for supporting providing the health services to the client, wherein the remote computerized terminal regularly synchronizes the computerized terminal with a remotely located computer server for verifying the provider providing of the health services to the client, wherein if the step of synchronizing fails, a process for trouble checking is implemented.

Further provided is method comprising:

providing a remote computerized terminal located in the client's home;

providing an enrollment interface for enrolling the provider using the remote computerized terminal, wherein the enrolling step includes the step of the client engaging the services of the provider for providing the health services to the client in the client's home, the engaging step including the step of collecting information from the client regarding the health services to be performed;

using the remote computerized terminal for verifying that the client engaged the services of the provider for providing the health services;

providing a provider interface on the remote computerized terminal adapted for accepting time information from the provider providing health services to the client at the client's home;

providing client interface on the computerized terminal for accepting validation information from the client for approving the time information accepted from the provider;

the computerized terminal collecting verification information for verifying that the time information accepted from the provider was entered with the terminal located at the client's home;

using a computer server remotely connected to the terminal via a communication network for formatting an electronic bill according to a predetermined format acceptable to a payment agency separate from the provider, wherein the remote computerized terminal regularly synchronizes the computerized terminal with the remotely located computer server for verifying the provider providing the health services to the client, wherein if the step of synchronizing fails, a process for trouble checking is implemented.

Also provided is a system including the computerized terminal and/or the computer server for providing any of the above methods or combinations of listed steps.

And further provided is a system for verifying provider services provided by a provider to a client in the client's home, comprising: a remote computerized terminal adapted to be located in the client's home for connecting to a communication network, the remote computerized terminal including at least one processor executing software for providing at least: an enrollment interface adapted for enrolling the provider using the remote computerized terminal, wherein the enrolling is adapted to include supporting the client engaging the services of the provider for providing the health services to the client in the client's home, the engaging step including the step of collecting information from the client regarding the health services to be performed, verifying that the client engaged the services of the provider for providing the health services, a provider interface adapted for accepting time information from the provider providing health services to the client at the client's home, a client interface adapted for accepting validation information from the client for approving the time information accepted from the provider, and collecting verification information for verifying that the time information accepted from the provider was entered with the terminal located at the client's home; a computer server remotely connected to the terminal via the communication network for formatting an electronic bill according to a predetermined format acceptable to a payment agency separate from the provider, wherein the remote computerized terminal is adapted for regularly synchronizes the computerized terminal with the remotely located computer server for verifying the provider providing the health services to the client, wherein if the step of synchronizing fails, a process for trouble checking is implemented.

Also provided are additional example embodiments, some, but not all of which, are described hereinbelow in more detail.

BRIEF DESCRIPTION OF THE DRAWINGS

The features and advantages of the example embodiments described herein will become apparent to those skilled in the art to which this disclosure relates upon reading the following description, with reference to the accompanying drawings, in which:

FIGS. 5A-5B show example screen shots for time entry for the example embodiment;

FIGS. 6A-6B show alternative example screen shots for time entry of an example embodiment;

DETAILED DESCRIPTION OF THE EXAMPLE EMBODIMENTS

Provided is a method and apparatus ("System") that facilitates the communication of health care information and tasks between and among users/employers/patients/customers ("Clients"), providers/employees/suppliers/caregivers ("Providers") State Agencies ("Agencies") and other third party agencies ("TPAs"). The providers can then be located in the client homes to provide health and medical services to the clients. This method and system can also be utilized in any situation where a provider of any type of services (including non-medical and non-health services) is providing those services to a client at a remote location (such as the client's home, place of business, travel destination, etc.), where the performance of those services and the presence of the provider is to be verified. Examples of such services might be equipment maintenance and/or repair, landscaping services, nanny or babysitting services, installation services, etc.

Potential services also include anything that can be done in a remote location, like a home (or a home-like setting) or at a business, and requiring central documentation and/or monitoring. Health care examples include personal care, home support, skilled care, medical care, non-clinical care, nursing, home health, hospice, palliative care, etc. Non-healthcare examples include, among others, house keeping (e.g., maid services), electricians, landscaping, contractors, etc. With the ability to be a time clock, take verification photos, verify with fingerprint scanning, log tasks, show status of documents, send internal messages, etc. the system can be used in quite a variety of settings and other features could be added to make it work in even more.

Figure 1:
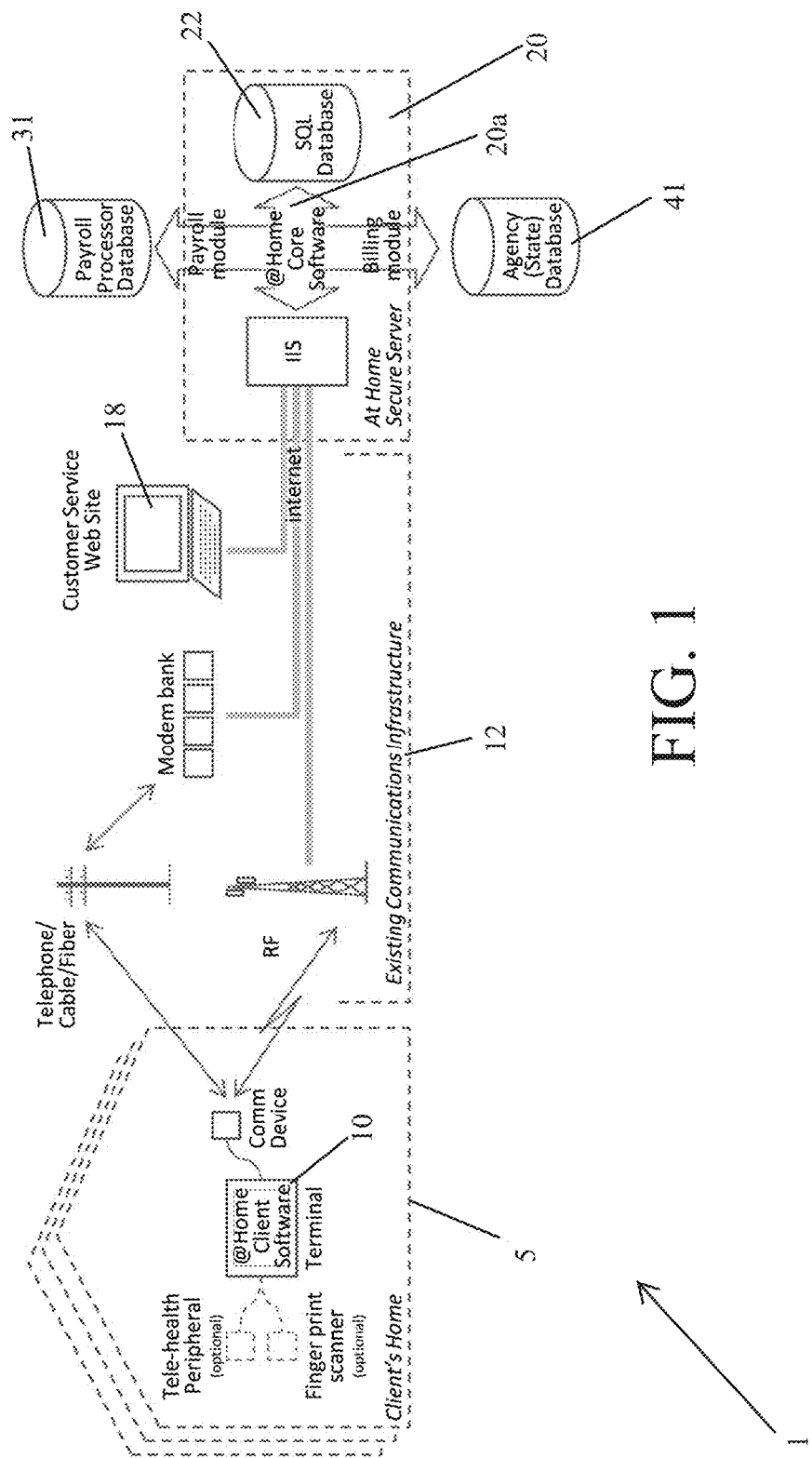
FIG. 1 is a schematic drawing of an example embodiment.
Figure 2:
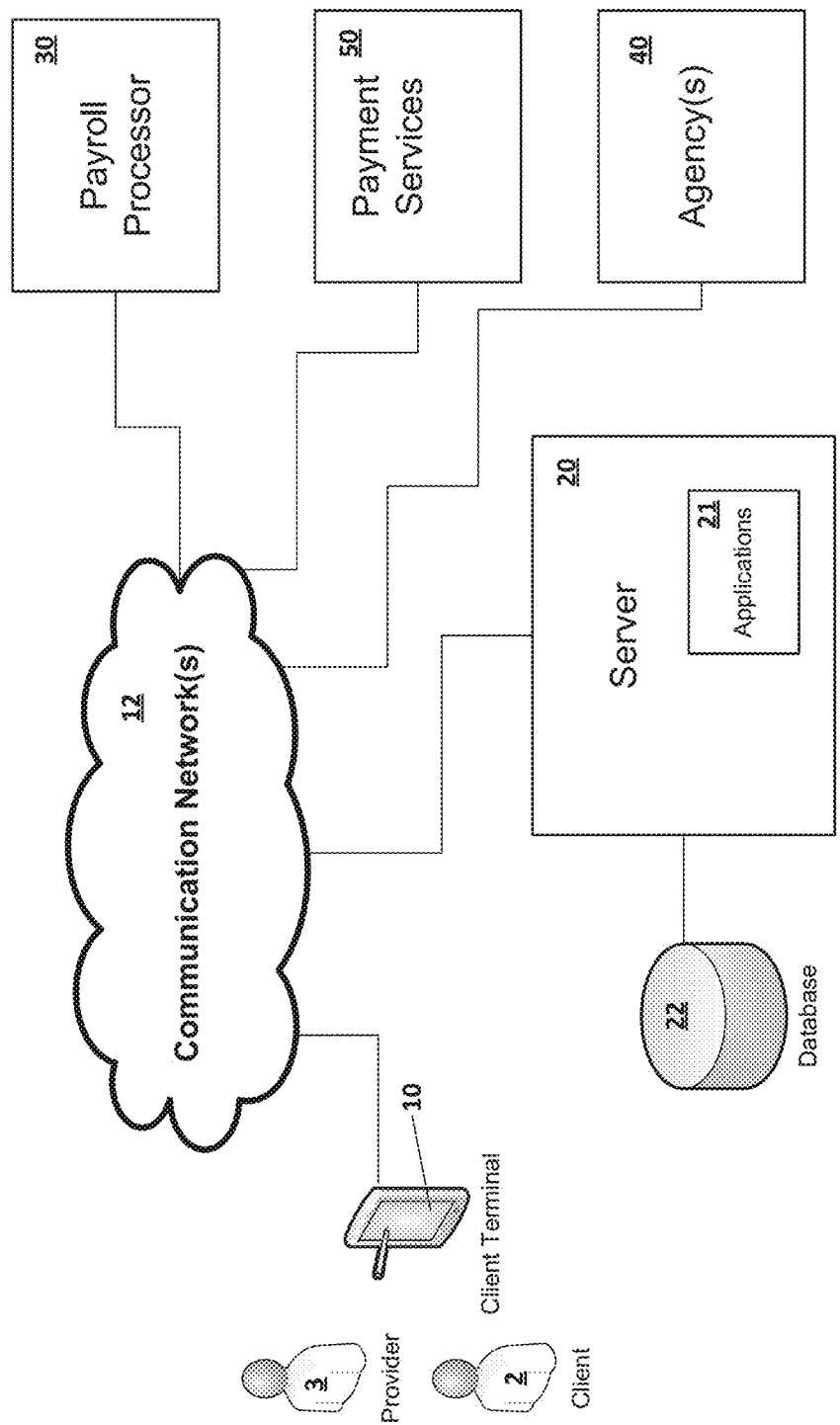
FIG. 2 is a schematic diagram of a simplification of the example embodiment of FIG. 1.

FIG. 1 shows a hardware configuration and implementation of an example system 1 for providing health services. FIG. 2 is a block diagram showing the primary components of the example system 1 in simplified form. Basically, the system 1 uses a client terminal 10 provided at least temporarily in the home 5 of a client 2. The client terminal 10 is connected to a server 20 via a communication network 12 (such as the Internet, a cellular network, POTS, WiFi, or some other network, for example, which may be a temporary connection). The server 20 is a computer server, such as a PC or similar hardware running an operating system such as Windows, Linux, or another commercially available system. The server 20 is connected to at least one database 22 (such as an SQL database, e.g., MySQL or MS SQL) and has a number of applications 21 for connecting to external systems. For example, payroll module 21b is provided for connecting to one (or more) payroll database 31 of a payroll processor 30, a billing module is provided for connecting to one (or more) agency database 41 of a Third Party Agency 40, and a core software module 21a is used for providing system functionality (as described below) and for integrating the other modules into a cohesive whole. A connection to a payment service 50 can be provided to directly accept client payments, where desired.

The client terminal 10 can be a laptop, tablet computer, smart phone, or some other device that is running an application for time card entry information and client approval (such as via a custom installed application or via a web browser, for example) and for connecting to the server 20. Both the client 2 and the provider employee 3 will typically have access to the client terminal 10 while it is in the client's home 5, which can either remain in the home of the client (as in the example), or which could alternatively be taken with the employee 3 to other client homes.

Figure 5A:
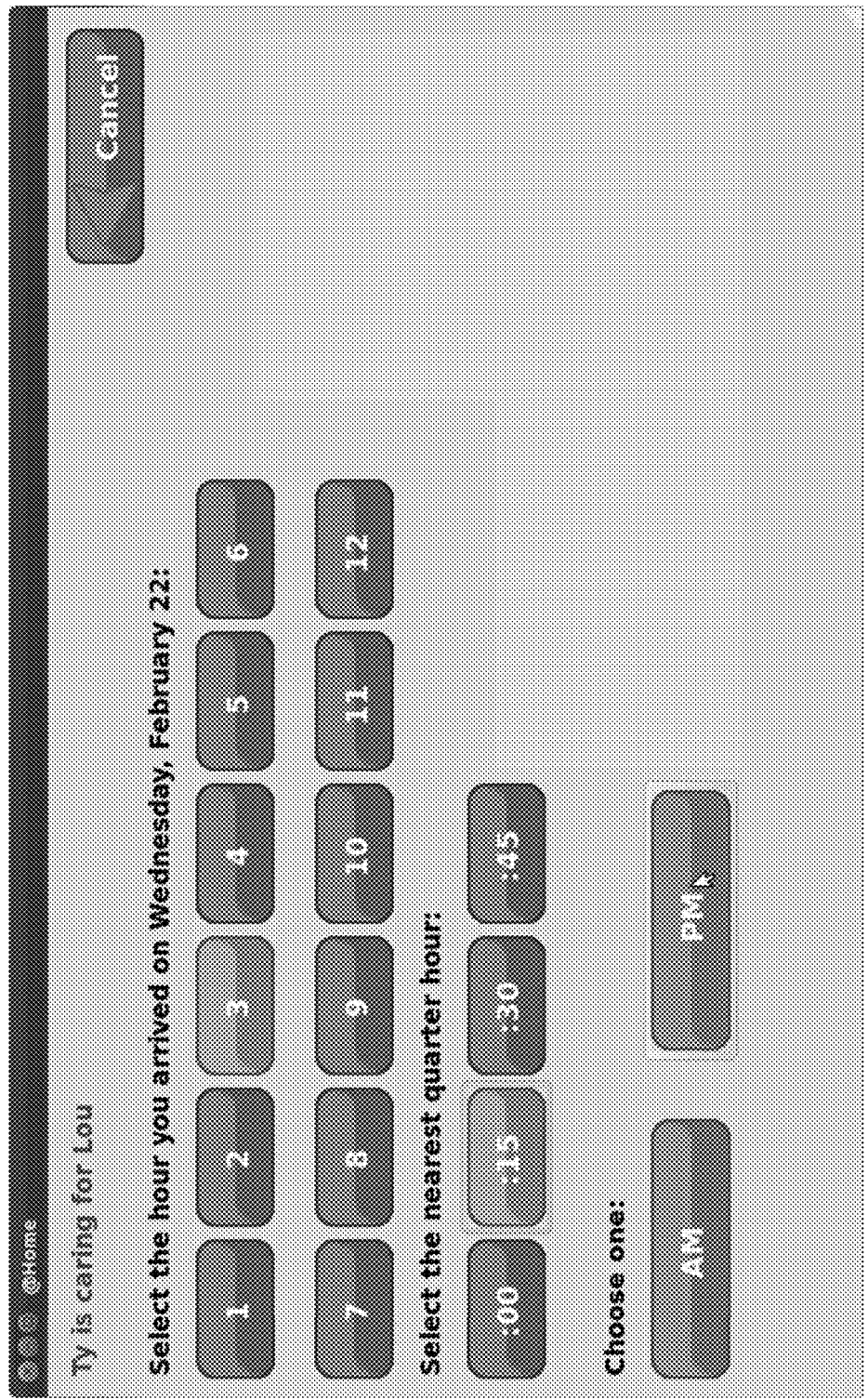
Figure 6A:
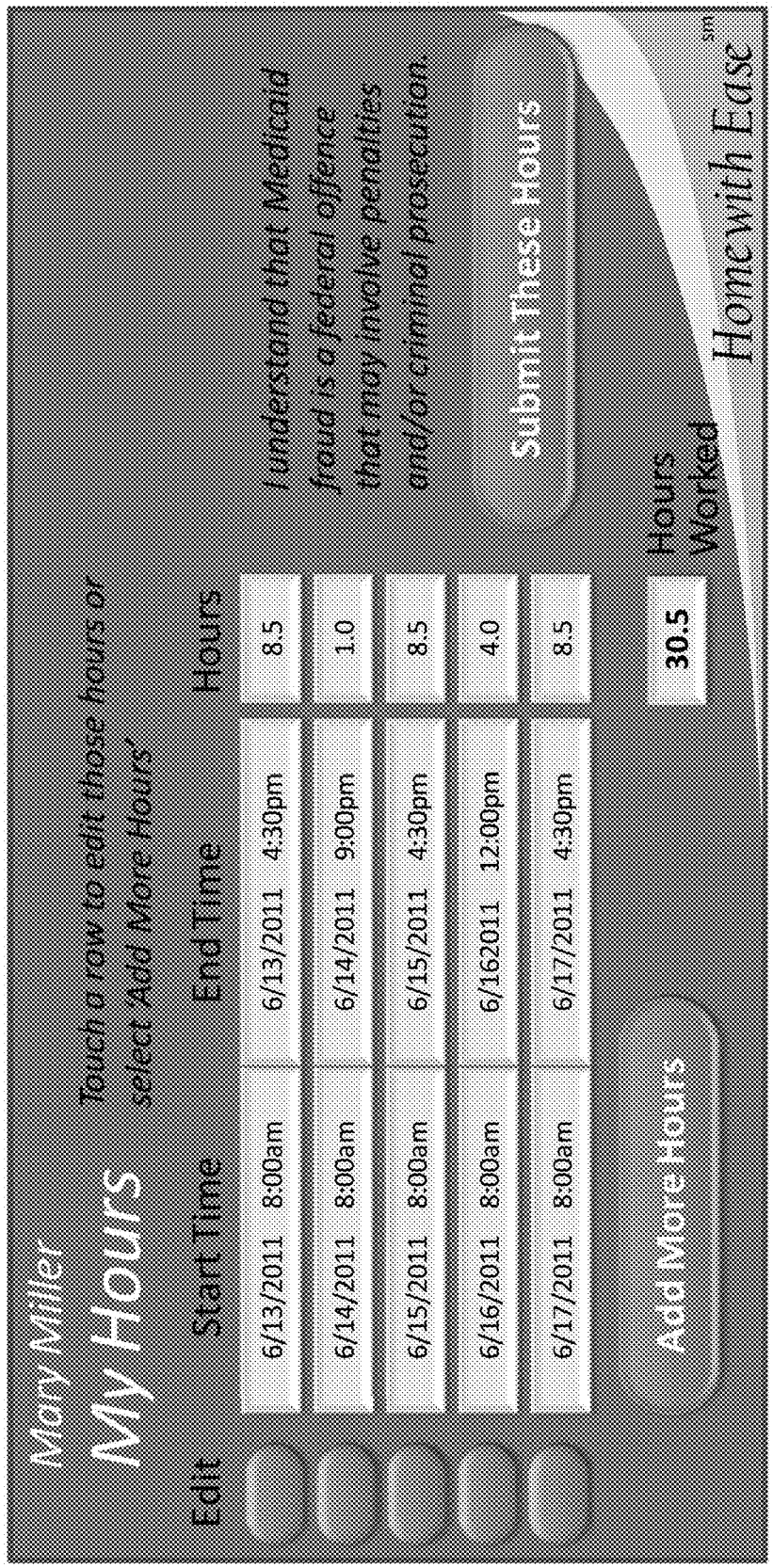

In the example system, one of the key features is an electronic "time sheet" that is filled out by the Provider. FIG. 5A provides one example screen shot of such a time sheet with wizard functionality, whereas FIG. 6A provides another different example screen shot of a time sheet where data can be entered directly. Such screen interfaces can be provided to the provider via a touch screen Terminal that is provided in the Client's home as the client terminal 10. FIG. 5A shows an example of a "wizard" that can be provided to walk the provider employee 3 through entering his or her hours, whereas FIG. 6A shows an alternative timesheet interface that allows the user to enter time worked.

The Provider, in the person of one or more provider employees 3, must be present in the home to submit his or her hours. The Terminal 10 collects data that is used to verify that the employee was actually in the home of the client 2 to provide the services. This can be done in a number of ways.

In the example embodiment, the terminal 10 takes a picture of the surroundings when the employee submits his or her hours for the particular client, to verify that the provider is actually providing the services to the particular client 2. This picture might be of rooms of the house 5, furniture or other items in the home, a picture of the client 2, or other photographed items. Alternatively, the terminal 10 can be permanently resident at the client 2 with its location determinable (such as by GPS or network location), or it may transmits some other location identifying information, such client identifying information (e.g., biometric information such as a fingerprint), or other means of verifying that the time was entered while the terminal was located at the particular clients home.

Figure 7:
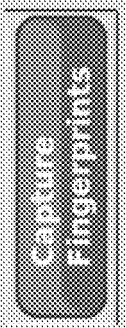
FIG. 7 shows an example screen shot for accepting a background check acknowledgement in the example embodiment.

In addition, the particular client can be asked to approve the time, such as by entering a signature, using biometric identification, a photograph of the client, or some other means, to further verify that the particular client affirms that the client received the services. This verification can use an acknowledgement screen for the client to approve the charges. Furthermore, the identity of the provider can be verified by a number of means, such as by using identification information and a photograph in a screen shot, such as is shown in FIG. 7, with the photo going where the "image" icon is found. Using this screen, the client can acknowledge that he or she has reviewed the background information of the provider. This also helps to ensure, with the client's support, that the person providing the services is actual the assigned provider, and not an imposter.

This approach to verification helps prevent fraud to some degree One could also provide other ways to clock-in/out as well using the system, because there are some services that are provided outside the home and/or start or end outside the home (e.g. grocery shopping), and thus the provider may be "on the clock" but not able to clock-in/out at the home of the client, or not able to obtain the client's approval, and thus a secondary non-verified approach to time clocking may be of limited utility in some circumstances. In some circumstances, the terminal can connect to the server immediately for certain events, such as to notify the office when a caregiver clocks in (or fails to clock in).

Alerts to the provider (caregiver) can be provided on logon, to the client on logon, and to the office (daily email) to (1) warn a provider not to exceed a certain number of hours this shift or it will be overtime (2) to warn a provider not to exceed a certain number of hours that day as that is all the time the client has authorized (3) to warn when provider documents or certifications will be expiring or are expired; and (4) to notify when a caregiver is eligible to be hired and is hired, etc.

Messaging functions can also be supported. For example, messages can be sent from the office (thru the server) or automatically by the system to any or all caregivers and/or clients. The ability to have the provider be randomly prompted during their shift to login to prove they are at the house can also be provided as a verification function.

The example System is composed of a terminal 10 including a touch screen capability ("Terminal") running a proprietary program applications 21 (the "Client Software") that is connected through a communications device communicating periodically over existing infrastructure with a secure server 20 ("Server"). The server 20 is running proprietary program, the core software 21a that, with modules 21b, 21c, and 21d, maintains the business, client, agency and provider information in a database 22. The System is designed to work with multiple (may scale to tens of thousands) of remote terminals communicating with a single Server (or multiple Servers if desired) for a centralized headquarters operation ("Back Office").

All of the elements of the example System are provided by the providing organization thus eliminating the need for Clients to have computers, modems, high-speed internet, or knowledge of these elements. The only exception is the communications infrastructure, in which case the System uses the existing communications mode available to the Client (such as WiFi, cellular data transmissions, and in most cases this can default to a plain old telephone system "POTS" connection).

The method of System design that is used for this example is to maintain industry standards, utilize components that can be swapped out, and to build cross-platform where possible from the start. This allows great flexibility to use almost any hardware and operating system.

These components are also what allow the system to be easily spread the load across multiple servers for great scalability while using low cost hardware.

The example System can be adapted to not allow hours to be billed that are not approved/funded by the Payer Organization (as discussed below). In the Enrollment process, there is provided an opportunity for the Client to elect to have the option to allow their Provider(s) to work more hours than those authorized by the State. In this case, an agreement with the Client to bill them directly, such as via credit-card or EFT, can be used to pay for such additional services, and thus a connection to third party payment services can be provided.

Client Terminal

The terminal 10 can be, for example, a commercially available, off-the-shelf tablet PC, laptop, smart phone, PDA, or similar device. A touch screen is a useful feature of such a device to utilize. The Terminal has a digital camera (internal or external) and may also be used as the primary communication device for other tele-health peripherals. Such a terminal is useful to avoid the need for any other external input device in the home (e.g. external keyboards, mice, etc.) whenever possible. In the example system, such terminals are provided as a part of the System by the organization running the system and will typically be preloaded with the Client Software at the Back-Office. The Terminal may be located in a Client's home or other place where care or services are rendered.

Under normal operation, the System synchronizes ("syncs" or a "sync event") with the terminal synchronizing with the Server on a nightly basis. Hence, as the terminal is updated, it is not required to update the server in real-time, but can do so periodically, such as nightly. In fact, the terminal need not be kept operating, but can turn on as needed to synchronize with the server. Being a normally scheduled event, the System, therefore, keeps track of all Clients, Providers and Terminals through the nightly sync events. If a Terminal does not sync, the System knows it the next day and trouble-shooting activities can be flagged to occur.

Alternatively, in particular where a permanent "always on" Internet connection can be maintained (such as using WiFi or cellular interface), synchronization can occur more often, or even in real-time whenever updated information to be synchronized is available. Synchronizing can also be triggered by actuating a synchronization button (which may be an actual button, or a touch-screen button or menu pull down, for example), such as whenever new data has been entered by the provider and/or client. Thus, the terminal can be provided with a "Sync Now" button to immediately upload some new data to the office (such as customer signatures) or download a change from the office (such as when clients move in or out of a house). This can be accomplished even with dial-up internet, allowing connections more than just nightly.

As an example, the Terminal can be any tablet or other computerized device that runs Windows, Linux (including but not limited to Ubuntu and Bodi), Apple OS or the Android operating system. The example software on the Terminal is built on a cross-platform library that can be compiled to run on Windows, Linux, or Mac. The Terminal software runs on x86 and ARM CPUs and can be modified to run on other CPUs as needed. The example terminal software is written in C++, including the SQLite database. The Terminal may also be connected to a fingerprint scanner or other biometric device for verification use.

Client Software on Terminal 10

The client software is proprietary software installed on the terminal 10 that is designed with Client capabilities in mind. The features of this software are described in more detail below.

Communications Networking

Referring again to FIG. 1, the terminal 10 can be connected to the network 12 by use of a communications device 11 (internal or external to the terminal 10) that is tailored to the existing communications infrastructure 12 that is available to the Client (including but not limited to a telephone modem, WiFi/WiMax adapter card, cellular adapter card, Bluetooth device, cable modem, or DSL modem, for example). Such a device might be a modem, WiFi access device or access point, Bluetooth access device, etc. The terminal 10 might connect to such a device via a USB connection or other serial port, or by Ethernet, or as an installed card or hardware, for example.

Server 20

An example server 20 includes hardware and software capable of servicing connections from multiple Terminals at a time and connecting them, through the Core Software, to the Database. The server also has the core software installed.

The Server 20 can be, for example, a high-end desktop PC running Windows 7 Professional 64-bit and containing a 3.10 GHz Intel Core i3 2100 CPU, 6 GB of RAM, and a 1 TB hard drive. This configuration is more than enough to handle a large number of terminals in the field doing nightly synchronization. Should the need arise, tasks may be split across multiple PCs before the need would arise to invest in higher-end servers.

Core Software 21

The core software is proprietary software capable of identifying a Terminal and synchronizing new data (from the Terminal or the Database) between the Terminal and Database. The Core Software also supports connections and synchronization to other agencies and Database maintenance tasks.

The Core Software can be, for example, written in ASP-.NET running on an IIS platform 21d. This configuration has been designed to be easily ported to run in Linux with PHP or others should the need arise to change platforms.

In addition to managing the SQL Database 22, the Core Software accesses an FTP site which allows for the download of updated software versions to the terminals.

SQL Database 22

A central repository (one or more databases) of all data collected from all Terminals 10, Customer Service web interface 18, and other agencies. Information in the Database 22 includes the status of all records including their stage of processing through the system.

The example SQL Database utilizes SQL Server Express Edition. All of the software is written with an API to each component, so that the API can be adjusted as needed. For example, if a Microsoft SQL Server Express were replaced with PostgreSQL, only the functions that border the SQL server would need to be changed, if at all (by using industry standards, such as industry standard SQL, changes can be minimized).

System Applications

The System 1 may be utilized for any application where a Client (or other authorized person/organization) must collect, track, authorize and/or communicate information to a Provider, Agency and/or TPAs (including but not limited to time, attendance, transportation, treatments, service plans, and work authorizations). The System 1 is frequently used in an arrangement where, for example, a State(s) agency requires a TPA to act in a capacity to distribute State funds to Providers on behalf of the Client. For example, such a system might support Medicare or Medicaid programs. The System may also be used in any private capacity where a Client and/or insurance provider desires accurate reporting, fraud prevention and simplicity.

Such applications include, but are not limited to, Home & Community Based Healthcare, Consumer Directed Healthcare, Managed Care, Home care agencies & registries, Disabled Persons (incl. Veterans), Child Care, Adult Community Centers, Nursing Homes, Mental Health & Psychiatric needs, and PACE programs.

For example, a typical application for the System is in the Consumer Directed Healthcare model wherein a Client and/or the client's family chooses to hire one or more healthcare workers (their "Providers" in this example). For Clients who qualify for these services to be paid by state Medicaid funds, the states require a third party to handle and disburse the state Medicaid funds. The Client is allocated a certain "budget" of hours and services by the state agencies and is sent to the Back-Office via fax, ftp, or email. This budget is entered into the System by the Back Office via the Customer Service Web Interface.

The Client may use the System to collect timecard and task completion details from the Provider. The Provider submits time worked via the Terminal in a time sheet format (this is distinctly different from a time clock), which are then forwarded to the Client for their review and approval (usually on a pre-defined payroll schedule: weekly, bi-weekly, etc.). The System will not allow the Client/Provider to use more hours or expenses than approved by the state agency. In some circumstances (e.g. private insurance, private pay or pre-agreed by the Client), when a Provider works more hours than pre-approved, the System will collect those hours and directly bill the Client (or another insurer) for those "over-time" hours. Once the Client approves and submits the time/tasks of the Provider, the System bills the various agencies/insurers (via B2B internet connection) as appropriate, and writes the checks for the Providers. With rare exception, by using this system this all happens paperlessly without fraud or error.

Operation

In its basic operation, the example System allows Providers to enter time and tasks into the Terminal and then forwards them to the Client for their approvals. Time and/or tasks are pre-authorized in the System, thus limiting inaccurate, un-authorized or fraudulent submissions. Once approved and submitted by the Client, remittance is processed by the Back Office headquarters operation.

Processes

Figure 3:
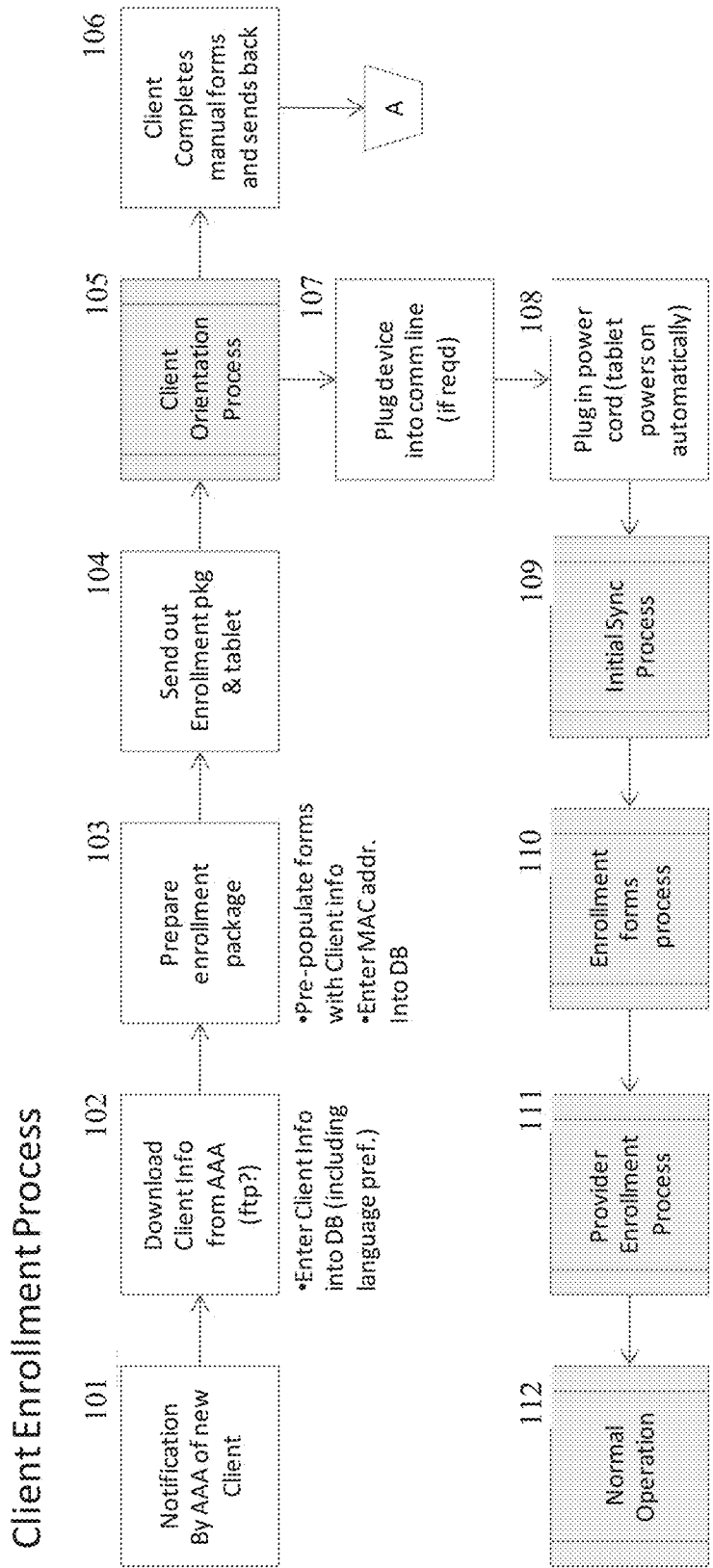
FIG. 3 is a flow chart showing an example of a client enrollment process that can be used in the example embodiment.

An example Client Enrollment Process is shown in the example flow chart of FIG. 3. This process is used when a new client has elected to utilize the System to administer his or her care and/or process payroll for his/her Providers. The primary steps of this example enrollment process shown in FIG. 3 are described below:

Step 101: Notification of new Client by Agency, Insurer or other authorizing source.

Step 102: The Client details are pre-loaded into the SQL Database. These details are provided by the Agency, Insurer or other authorizing source and include basic Client information (name, address, SSN, phone number, etc.) along with the details of the authorized work (Individual Service Plans, Work Orders, or other forms of Agency authorization).

Step 103 Required paper forms are printed (with the Client details pre-populated) and packaged with the Enrollment Guide and Terminal in a carton. The serialized unique identifier of the Terminal (the "Unique hardware identifier") is entered into the SQL Database and keyed to the Client. An example list of such forms for the state of Pennsylvania are appended to the end of this disclosure.

While most of the information is pre-populated by the Back Office or input directly into the Terminal, some forms (e.g. Power of Attorney) may require having a direct Client signature.

Step 104: The carton is sent to the Client (or may be hand delivered by a Relationship Manager).

Step 105: Upon receipt, the Client opens the carton and removes the Enrollment Guide. The Client may review the Enrollment Guide or be guided through the Enrollment Process by a Relationship Manager.

Step 106: The Client reviews and signs any required paper forms and forwards them back to the Home Office.

Step 107: Following the Enrollment Guide, the Client plugs the Terminal into the phone line (or other Communications Source as available).

Step 108: The Client plugs the Terminal into the power outlet. The Terminal automatically powers up.

Step 109: The Terminal performs an Initial Sync process with the SQL Database to download the pre-loaded Client information as well as software updates.

Step 110: The Terminal then prompts the Client for any additional information that may be required (see end of disclosure for representative forms). Additional information is uploaded to the SQL Database at some point where activity is low, such as the following midnight, and all actual paper forms that must be submitted in paper are printed and mailed to the appropriate Agencies and/or filed by the Back-Office. Other data is processed by the Back Office via online application or automatic updates through Business to Business ("B2B") data exchanges (examples include PA-100, State Unemployment Application, Federal Tax ID, etc.).

When all the forms have been processed and returned to the Back Office, the Client's account is authorized.

Figure 4:
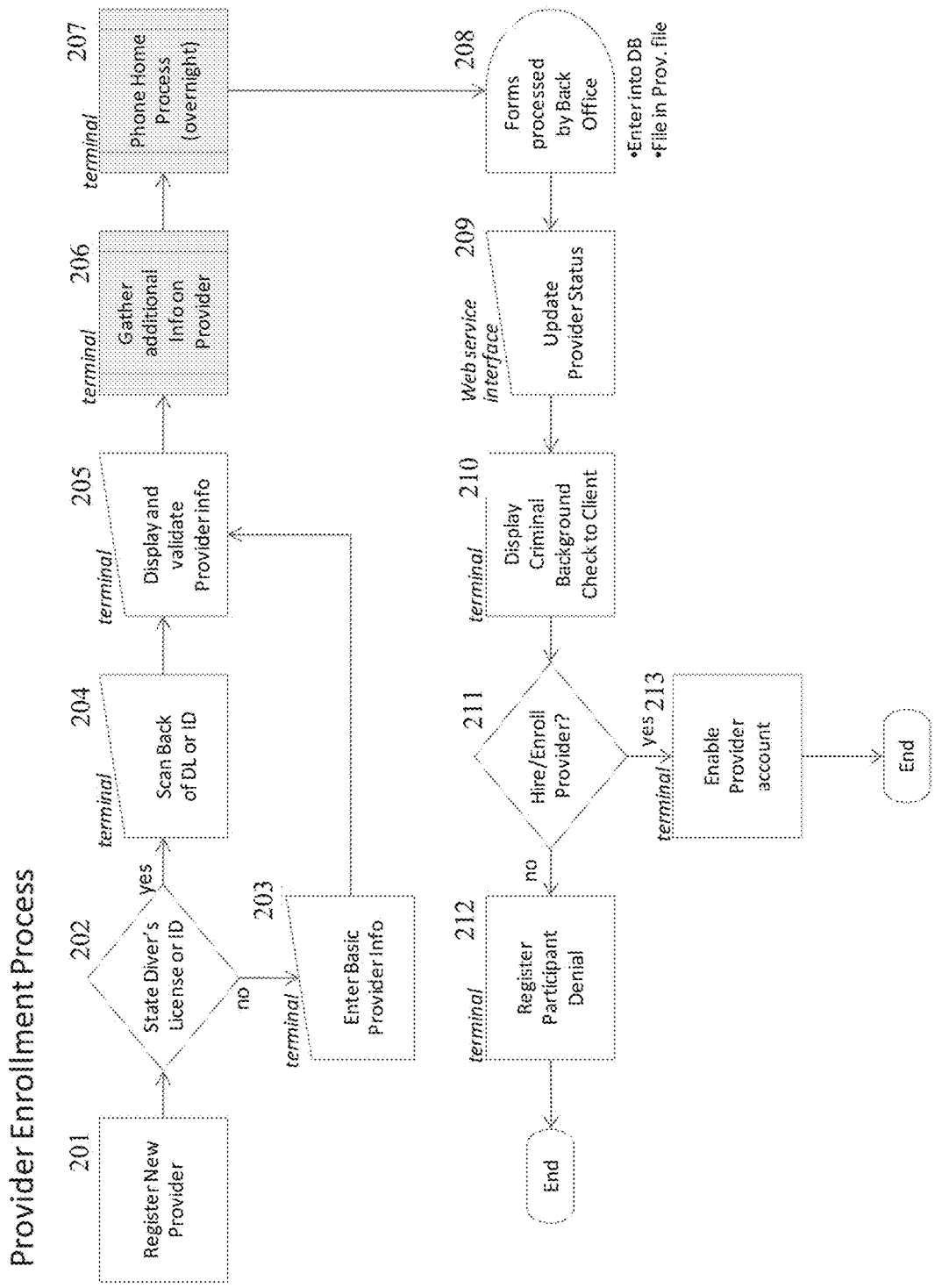
FIG. 4 is a flow chart showing an example of a provider enrollment process that can be used in the example embodiment.

Provider Enrollment (FIG. 4)—When a Client wishes to hire a new or additional Provider, the process of the flow chart of FIG. 4 can be used, as follows:

Step 201: A Client has a need or desire to register a new Provider.

Step 202: If the new Provider has a State Driver's License or State issued ID it may be used to automatically enter information Step 203: If the Provider does not have a DL or ID, their basic personal information must be manually entered.

Step 204: The back of the Provider's DL/ID is held up to the Camera and captured by the Terminal. The Provider's basic personal information is decoded by the Client Software from the 2D bar code on the back of the DL/ID. At writing, 39 states use this same bar code.

Step 205: The Provider's data is displayed and the Client must confirm that it is correct.

Step 206: Additional details are then input via the Terminal by the Client (the Client may elect to allow the Provider to enter the information).

Step 207: The Terminal uploads the Provider details to the SQL Database overnight.

Step 208: The forms are printed and processed by the Back Office.

Step 209: As the forms are processed and returned, the status of the forms is updated in the SQL Database. A copy of each form is filed in the Participant File. Upon nightly synchronization, the statuses of the Provider's forms are updated on the terminal.

Step 210: Once all the forms are completed, updated, and filed the criminal background check is displayed to the Client (at their prompting) along with any other requested details.

Step 211: The Client is prompted as to whether or not they wish to hire/enroll this particular provider.

Step 212: If NO, the SQL Database is updated to reflect denial by this Client.

Step 213: If YES, the Provider's profile is enabled on the Terminal.

When all the forms have been processed and returned to the Back Office, the Client's account is authorized.

Figure 8:
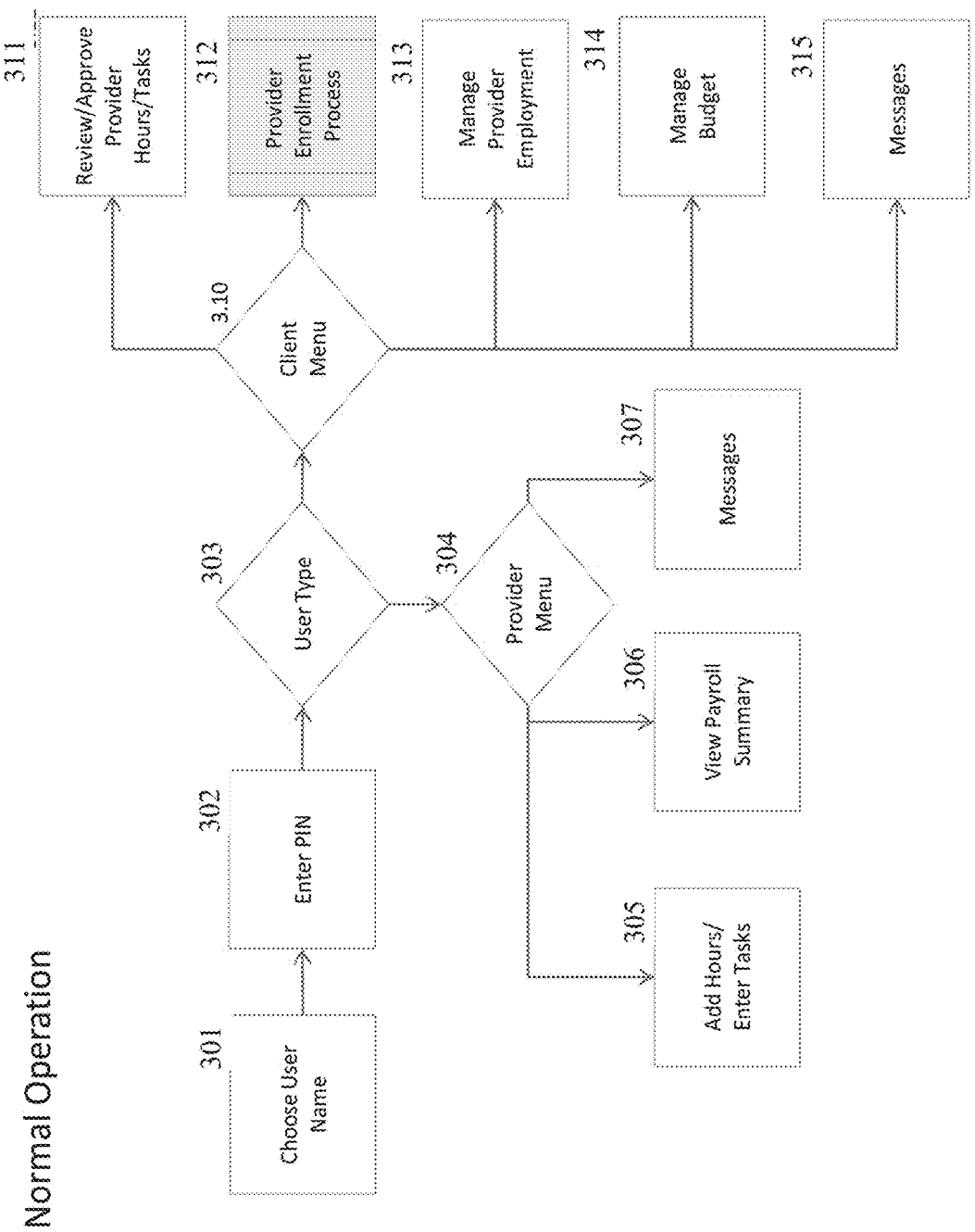
FIG. 8 is a flow chart showing an example of a normal operation that can be used in the example embodiment.

Normal Operation (FIG. 8)—Default operation of the System is shown in the flowchart of FIG. 8 as follows:

Step 301: The Terminal displays the registered Client(s) and Provider(s) and the current user may select one. The Client is always the first person displayed in the list of users. If the Terminal is connected to a biometric reader device, that input may be used to automatically login the user. For example, if a fingerprint scanner is attached, the user simply touches the scanner, the Terminal recognizes the user and advances to step 303

Step 302: The user enters their personal identification number (PIN) which acts as a digital signature. The programs advances to the next step immediately upon entering the final digit of the PIN (i.e. there is no 'Enter' or 'Next' button to eliminate superfluous steps). Care givers and clients can be alerted with pop-up notifications upon logging into the terminal that they are reaching limits of service by day, week or pay period. Upon clearing the notification with an acknowledgement ("OK" button or otherwise) a record is kept that they have acknowledged the alert.

Step 303: Based on user type (determined at login) the Terminal will display either a Client menu or a Provider menu.

Step 304: The Provider menu consists of options to Enter New Hours/Tasks or View a Payroll summary.

Step 305: A Provider may enter time and or tasks into the Terminal. After signing into the Terminal with their PIN, they can enter time/tasks into a time sheet form (see FIG. 5B or 6A). Data entry is accomplished with simple controls on the touch screen Terminal. The Provider is then prompted with a fraud warning before final submission. Upon confirmation, the Terminal can capture a camera image of the Provider and stores it along with the timesheet data. Alternatively, should the third party agency and/or State desire, the Terminal can configured to act as in "time clock" mode vs. "time sheet" mode whereby the Provider must clock-in and out when they arrive and leave from the Client's home (see FIG. 5A).

Step 306: The Provider may view any prior pay period including hours claimed, hours authorized, hours paid, pay rate, tax withholding and other payroll details.

Step 307: The Provider may view messages sent from the Back Office. These may be specific to the Client or Provider or they may be broadcast messages to all users. Additionally, some forms may require periodic updating (e.g. annual certifications). The Provider will receive a notification that a form must be updated here. If the form is not updated by its expiration date, the Provider will be unable to enter shifts until the form is updated.

Step 308: In some embodiments, The Client may bring up time/tasks claimed in the current pay period or prior pay period for approvals. In other embodiments, this step may be omitted.

Step 309: In some embodiments, The Client may add a new provider through the Terminal. In other embodiments, this step may be omitted.

Step 310: The Participant menu allows the Client to review and approve time/tasks submitted to them from the Provider(s), review the enrollment status of their new Provider(s), Enroll a new provider and to manage their budget.

Step 311: The Client may bring up time/tasks claimed in the current pay period or prior pay period for approvals. If they determine that they time/tasks are acceptable, they approve them and then when done submit all of the approved hours (q.v. FIG. 4). The Client is prompted with a fraud warning and asked for a final acknowledgement. Upon this submission, an image may be captured by the camera and stored along with the approval.

Step 312: The Client may add a new provider through the Terminal. The Client may add a new provider through the Terminal. The forms/paperwork/certifications used to enroll an employee can be shown along with the status of each form. For example, one required document may be a background check which can show statuses of open, received, in-process, complete, rejected or failed. Other information may also be shown on this screen including an image of the caregiver.

Step 313: The Client may review the status of their new Provider(s) enrollment. This will display a photo of the Provider, the status of the various forms, expiration of forms and, when all of the forms are complete, will allow the Client to hire/enroll the Provider. The Client may also set the pay rate of the Provider within the limits established by the Back Office. Additionally, some forms may require periodic updating (e.g. annual certifications). The Provider and Client will receive a notification via the messaging service that a form must be updated here. If the form is not updated by its expiration date, the Provider will be unable to enter shifts until the form is updated.

Step 314: The Client may also view and manage the budget for programs such as Cash and Counseling, Services My Way, or other Consumer directed program. The care plan prescribed by the Agency can be displayed to the Client via the terminal. Limits of service/care may be entered into the system so that custom alerts can warn when the Caregiver (provider) is approaching the allocated time limits prescribed in the care plan.

Step 315: The Client may view messages sent from the Back Office. These may be specific to the Client or Provider or they may be broadcast messages to all users.

Figure 9:
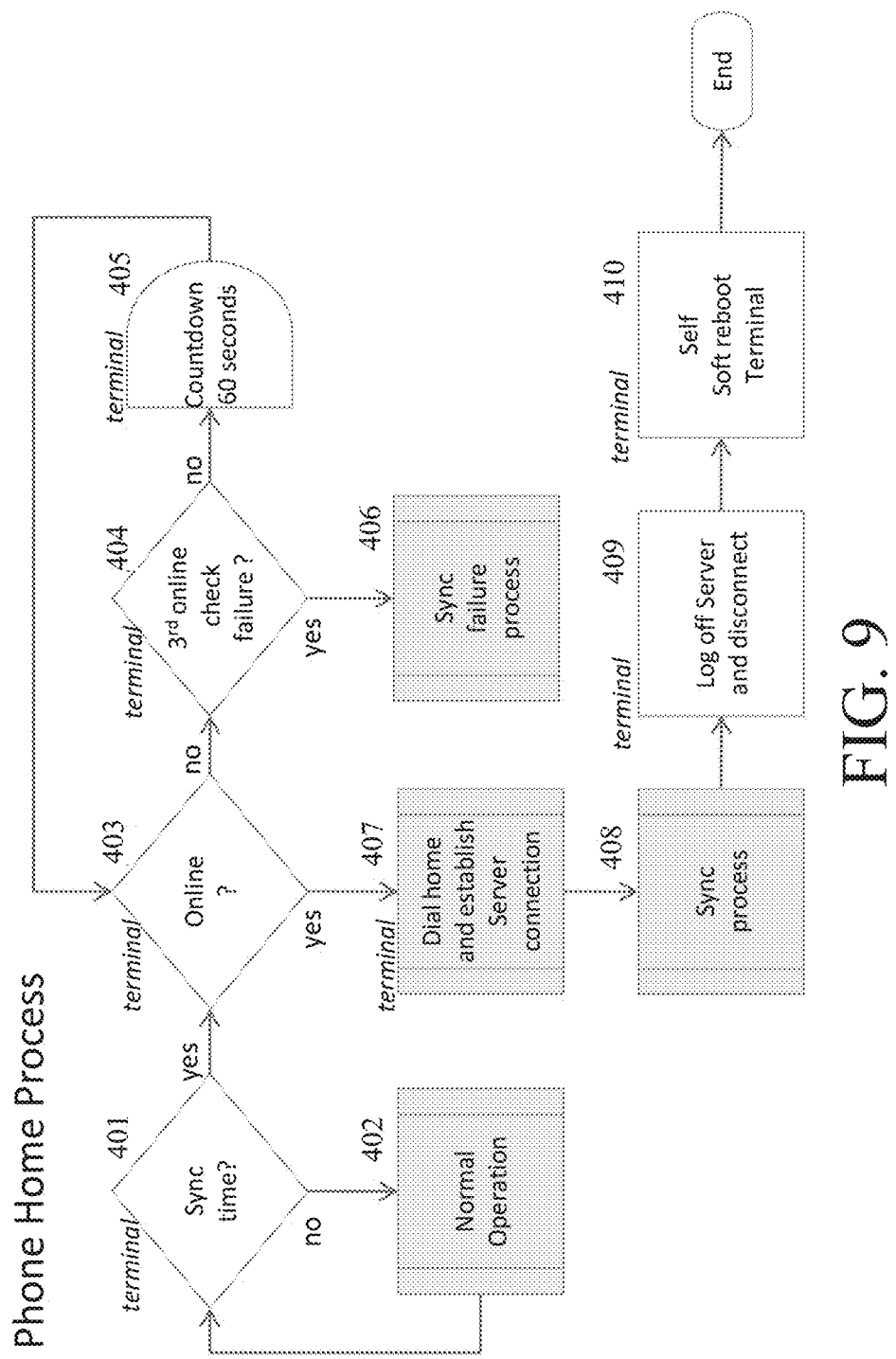
FIG. 9 is a flow chart showing an example of a "Phone Home" process that can be used in the example embodiment.

Phone Home Process—This process, shown by the flow chart of FIG. 9, can be performed at a nightly scheduled time, and has the following steps:

Step 401: Is the current time the scheduled sync time for this Terminal?

Step 402: If not, return to Normal Operation of Terminal.

Step 403: Check the communication connection for online

Step 404: If online failure check three times before indicating failure.

Step 405: Wait between tries.

Step 406: If the connection has failed three times, the Terminal will indicate a communications failure the next time any user awakes it from screen saver mode. On the Server side, the System will know that there was no nightly sync from this device and the Back-Office will attempt to contact the Client to help diagnose the communications failure. No data is lost.

Step 407: Once communication is established the Terminal will dial out through the communications path and establish connection with the At Home Secure Server Step 408: The Terminal and the SQL Server will synchronize user data, software revisions, and Terminal graphics.

Step 409: Once data communication is complete, disconnect from communication line.

Step 410: Terminal reboots itself to update software, drivers, etc.

Synchronization Process

Figure 10:
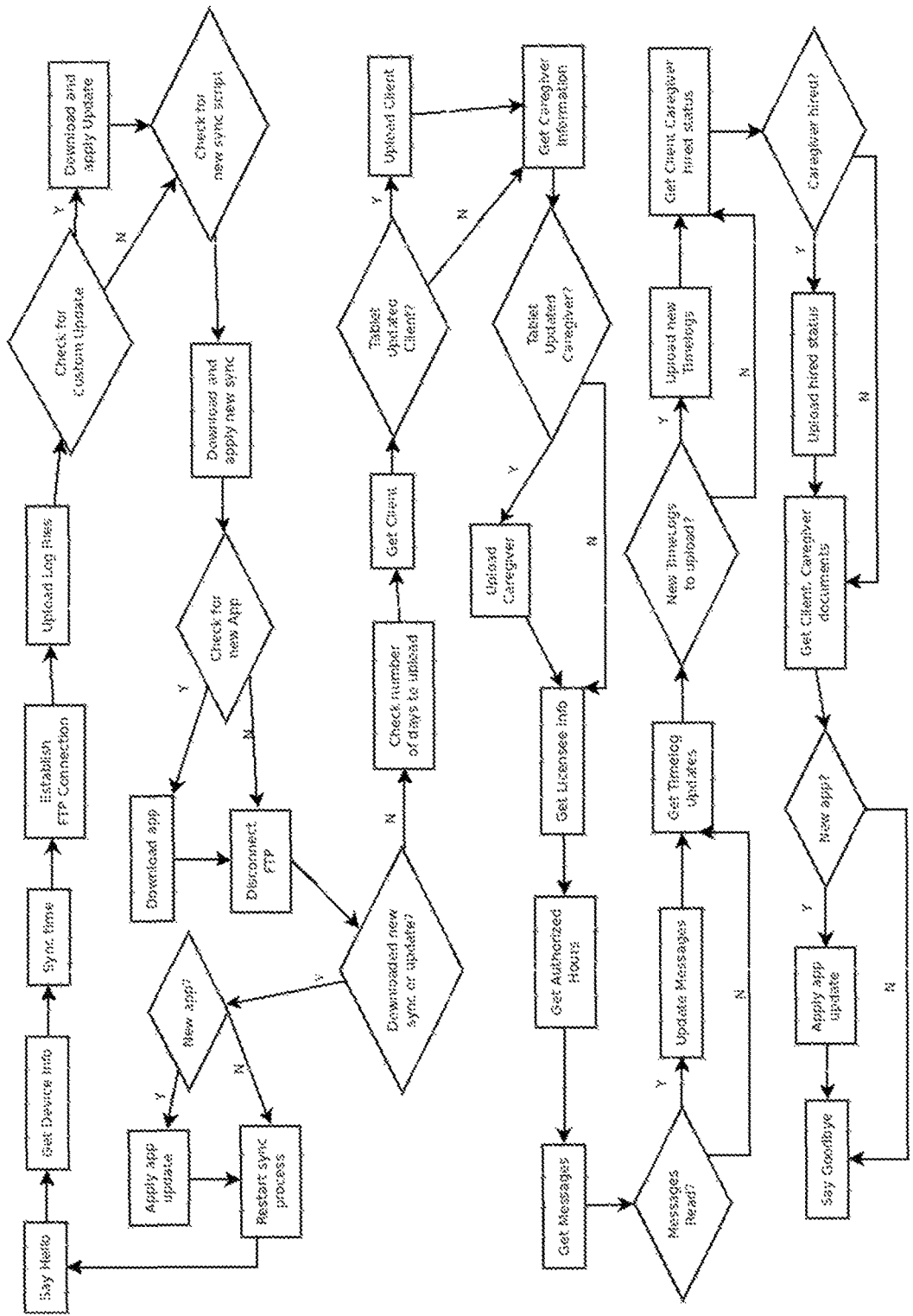
FIG. 10 is a flow chart showing an example of a synchronization process that can be used in the example embodiment.

The Synchronization Process (Sync Process) of step 408 of FIG. 9 is outlined in FIG. 10 in detail.

Figure 11:
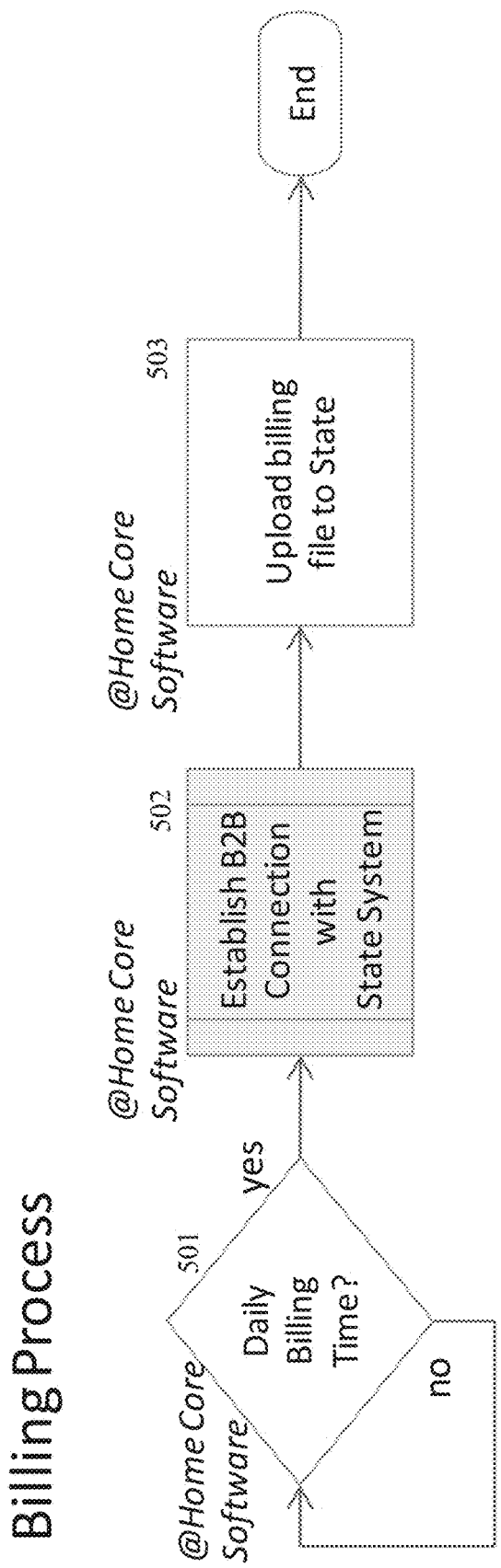
FIG. 11 is a flow chart showing an example of a billing process that can be used in the example embodiment.

The Billing Process is described in the flow chart of FIG. 11, showing the following steps:

Step 501: The Core Software will bill the Payer Organization daily.

Step 502: Establish a B2B connection with the appropriate Payer Organization. If there is no available B2B service from the Payer Organization, the Back-Office will submit billing via available means.

Step 503: Upload the billing file to the Payer Organization.

Figure 12:
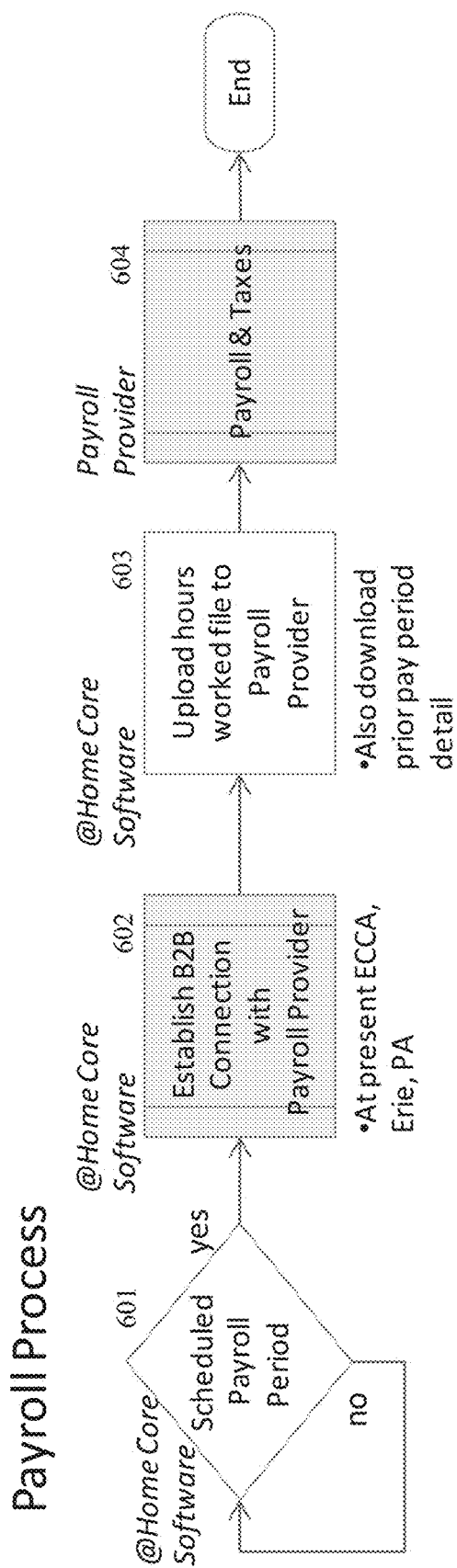
FIG. 12 is a flow chart showing an example of a payroll process that can be used in the example embodiment.

The Payroll Process is shown by the example flow chart of FIG. 12, having the following steps:

Step 601: The Payroll process will be run per a defined schedule (weekly, bi-weekly, etc.)

Step 602: Establish a B2B connection with the Payroll Provider

Step 603: Upload Provider hours worked file and download prior pay period details Step 604: The Payroll Provider is responsible for issuing paychecks and making all tax remittances.

Figure 13:
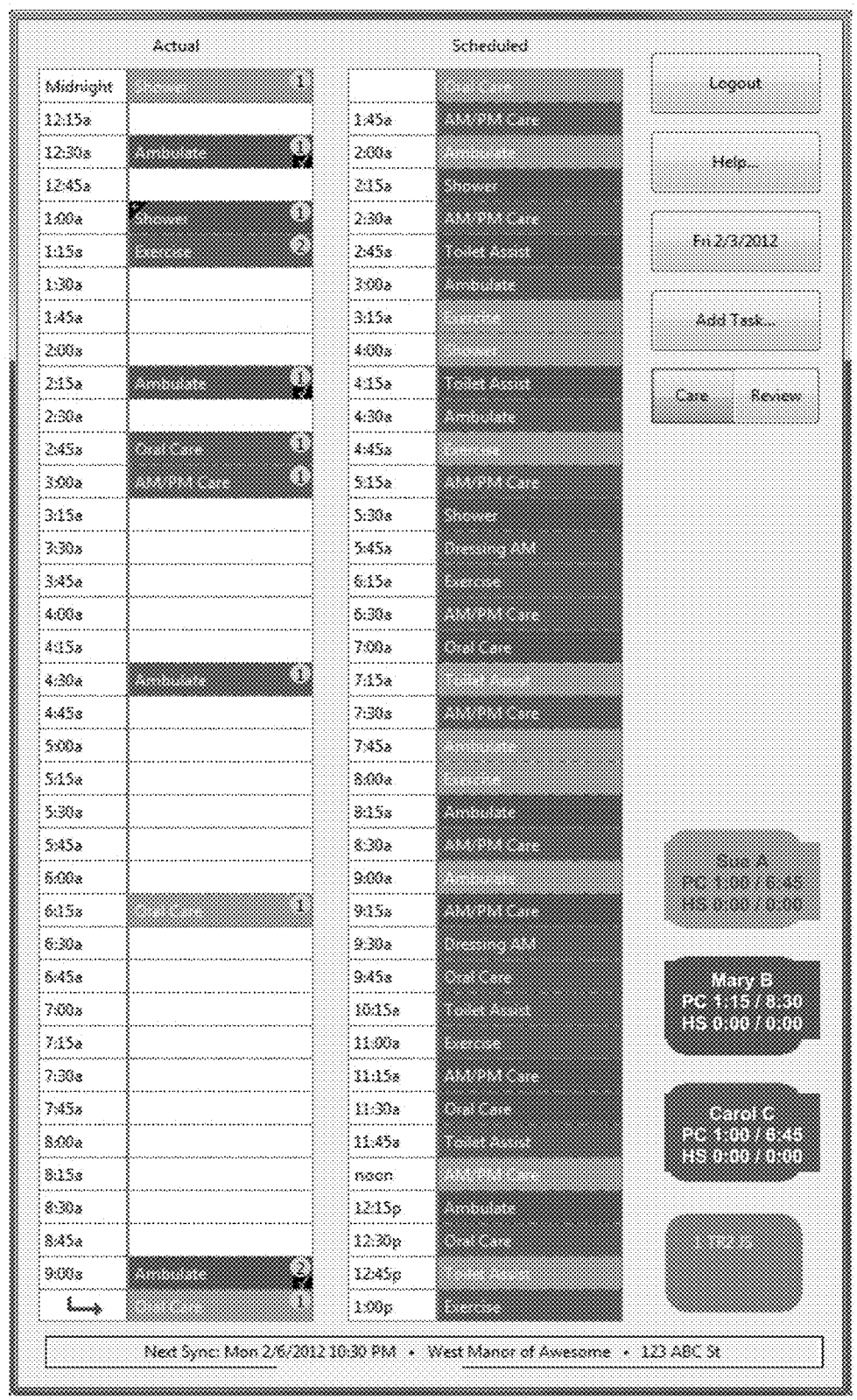
FIG. 13 shows an example screen shot for a Task Interface screen for the example embodiment.

A Task Interface screen shot is shown in FIG. 13. The Task Interface is a unique methodology used to record exactly what care task took place at what time during the day. A list of scheduled tasks is displayed in a column on the client terminal with an 'actual' timeline column where tasks are moved when they are completed. The process of using such a task list is described in more detail below:

Task List: Via the Customer Service Web Portal a master task list is created to reflect all possible tasks that will be tracked.

Task/House Schedule: From the Task List a customized schedule by day of the week is created for each client. In the case where multiple client reside in a home or activity center a house schedule can be created showing multiple clients tasks throughout the day Add Task: If a task is not included for a Client on that day but is performed, the Caregiver may add a task from the task list via the terminal. Added tasks appear in the Scheduled task column and are denoted with a '+' sign.

Completing a Task: To document when a task has taken place the caregiver can drag-and-drop with the touch screen from the scheduled list of tasks to the actual timeline column in the appropriate timeslot.

Multiple Clients: Client are designated by color

Multiple Caregivers: Caregivers are designated by number.

A caregiver may not drag-and-drop a scheduled task on top of their own existing actual task within the same timeslot (i.e. two tasks cannot be completed at the same time by the same caregiver). A caregiver may drag-and-drop a scheduled task on top of a different caregiver's existing actual task within the same timeslot. There may be circumstances where multiple caregivers are working within the same facility thus completing tasks at the same time.

Client Task Confirmation: Caregivers can review the completed schedule with the Clients and have the Client acknowledge those activities took place at the recorded times. The Client can acknowledge with a PIN or via a biometric device (e.g. fingerprint scanner). Once acknowledged by the Client, tasks may not be edited, moved or deleted.

Tablet View: Within the Customer Service Web Portal the data may be viewed just as it is displayed on the terminal.

Advantages/Unique Features of the System:

(1)—Ease of Use. Clients may or may not have experience with computers. Computers can often be intimidating to elder populations who have not grown up with them or been exposed to them. The ubiquitous internet that is so useful and easy for many in our society can be confusing and daunting for the Clients. The System specifically does not require knowledge of computer systems, networks, internet, URLs, websites, etc. Nor does the System require any special knowledge, skill or dexterity to use a computer mouse or other input peripheral. The touch screen device ("Terminal") takes all user input through the touch screen and/or the camera guided by simple on-screen cues. In addition to its simple and easy to use interface, the Terminal with the Client Software is designed with a poka-yoke input process (i.e. fail safe or mistake-proof) that eliminates transcription errors, rework loops and mistakes.

(2)—Flexible Communications Path. Frequently the population of Clients may not have high speed internet connections and/or internet access although they will have a hard wired traditional telephone (POTS). The System specifically does not require an always-on high-speed internet line but is configurable to utilize the Client's existing communications method: high-speed internet connections when available, cellular communications or POTS lines. In any case, the System utilizes a "Store and forward" methodology that does not require real-time access to a database. Client and Provider interactions are stored on the User Interface and forwarded to the Database nightly. This "Store and Forward" synchronization eliminates always-on costs.

(3)—Fraud & Theft Prevention. Unfortunately fraud and abuse are a reality in Medicaid, Medicare and private insurance. The System has a secure login for Clients and Providers to ensure privacy and security. Further, since the system is not on-line, the Terminal password can be a simple personal identification number (PIN) being much more user friendly than internet login passwords. Alternatively the System may employ a biometric read (e.g. fingerprint scanner) to provide an additional level of security. In addition to the unique login/PIN or biometric reader, the System may capture an image of the individual submitting hours, or tasks authorizing payment. Capturing an image is at the discretion of the business using the system. This image is collected and stored in the record for fraud investigations and helps to ensure that the Provider is present in the Client's home. Additionally, the camera may be used for biometric facial recognition to automatically login a Client or Provider.

The System also deploys a two-level check and balance between the Provider who inputs their hours and the Client who approves the hours.

(4)—Simple Provider Enrollment. Clients have a need to enroll several Providers over time. Clients have to collect several different forms (q.v. Appendix A) in order to enroll a new Provider. This can be a time consuming, error prone and potentially fraudulent process. The System allows Provider information to be collected via the Terminal with the required forms then being processed in the Back Office on behalf of the Client. Common information (e.g. name, address, etc.) is collected only once instead of the Client having to fill this same information on many forms. To further ease the collection and entry of Provider information, the System utilizes the built in camera to capture and decode the 2D barcode located on the back of a Provider's Driver's License or State ID. This eliminates transcription/keystroke errors and prevents the opportunity for fraudulent applications.

(5)—Distribution Method and Client start-up. As stated previously, computers (or electronic devices in general) may be intimidating to some Clients. In home installations with many wires, poorly written instructions, references to obscure components, start-up and login procedures and other technically complicated jargon can confuse even well-educated Clients. The System requires no manual inputs from the Client to initiate care. The Terminal is pre-loaded with Software at the Back Office or other third party packager with all of the peripherals and wires pre-connected and secured by the housing (q.v. section 6). When notified of a new Client, the Client's information (provided by the Agency) is pre-loaded into the Database and linked to the Unique hardware identifier of the device. The box containing the matching Unique hardware identifier is shipped directly to the Client. Upon receipt, the Client need only to open the box and plug the Terminal into the telephone line (or other pre-determined comm. path as outlined in section 2 above) and plug the power cord into the power outlet. The Terminal powers-on automatically and synchronizes with the database (with the Unique hardware identifier being the unique identifier) and downloads all of the Client data.

(6)—Robust Terminal. The Terminal is packaged in a frame/housing that secures all of the device connections and peripherals as well as proving a stable base. The housing is affixed to the Terminal with a permanent adhesive to assist in theft prevention. Any wires, connections, Communications Devices are secured with a permanent adhesive within the housing so that they cannot fall out or be disconnected. This helps to ensure that simple wiring connections do not delay service delivery or confuse the Client.

Some documents/certifications may require periodic updates or renewals. The system can track when any of these are due to be updated or renewed, alert the caregiver (and client) when any of them are approaching their due (expiration) date(s) and, if the documents/certifications are not updated, prevent the caregiver from clocking hours, where necessary.

Partial list of Example Forms:

For illustration purposes we have referenced some of the applicable forms for the state of Pennsylvania:

Personal Representative Form (if needed)
Agreement between Consumer/Employer & Personal Assistant Consumer Addendum to Agreement between Consumer/Employer & Personal Care Assistant
Employer Appointment of Agent (Form: 2678)
PA Enterprise Registration Form (Form: PA-100)
Application for Employer Identification Number (Form: SS-4)
Workers Compensation Appointment of broker Agent (FEA-70-6-1)
Elect Domestic Employees (LIBC-510)
Workers Compensation Notice of Rights & Responsibilities (FEA 70-6-2)
PA Unemployment POA (UC-884)
Statement of Agreement and Compliance
Reporting Agent Authorization IRS 8655
Wage and Tax Statement IRS W-2
Tax Information Authorization IRS 8821
New Hire Reporting Form PA BUR 1575
Employer's Report for Unemployment Compensation PA UC-2
Employer's Quarterly Report Of Wages Paid To Each Employee PA UC-2A
Employer's Report of Employment and Business Changes PA UC-2B
REQUEST FOR CRIMINAL RECORD CHECK SP-164
PENNSYLVANIA CHILD ABUSE HISTORY CLEARANCE CY-113
Employment Eligibility Verification US CIS 1-9
Employee's Withholding Allowance Certificate IRS W-4
Request for Taxpayer Identification Number and Certification IRS W-9
Employer's QUARTERLY Federal Tax Return IRS 941
Employer's Annual Federal Unemployment (FUTA) Tax Return IRS 940
Employer Deposit Statement of Withholding Tax PA 501
W-2 Transmittal REV 1667
Employee's Nonwithholding Application Certificate REV 419
Miscellaneous Income IRS 1099-MISC
Annual Summary and Transmittal of U.S. Information Returns IRS 1096
Transmittal of Wage and Tax Statements IRS W-3
Determination of Worker Status IRS SS-8

As will be appreciated by one of skill in the art, examples of the disclosed innovations discussed above may be embodied as a method, a system, a computer program product, software executing on a processor/computer, or a combination of the foregoing. The example embodiments discussed herein may take the form of an entirely hardware implementation, or an implementation that combines software (including firmware, resident software, microcode, etc.) and hardware components. The software may be stored on a computer usable storage medium having computer-usable program code embodied in the medium, which may be packaged as a computer program product. Any suitable computerized device comprising a processing component (e.g., a processor) and a computer readable medium may be utilized for providing example embodiments.

Generally, a computer usable or computer readable medium may be any medium that can contain, store, communicate, propagate, or transport the program for use by or in connection with the instruction execution system, platform, apparatus, or device. The computer usable medium may include a propagated data signal with the computer-usable program code embodied therewith, either in baseband or as part of a carrier wave. The computer usable program code may be transmitted using any appropriate medium, including but not limited to the Internet, wireline, POTS, optical fiber cable, radio frequency (RF) or other means. The computer readable medium may comprise, for example but not limited to, an electronic, magnetic, optical, electromagnetic, infrared, or semiconductor system, apparatus, device, database, or propagation medium. More specific examples of the computer readable medium would include, but are not limited to, a computer diskette, a hard disk, a random access memory (RAM), a read-only memory (ROM), an erasable programmable read-only memory (EPROM or Flash memory) which may be internal or external, permanent or removeable, a compact disc read-only memory (CDROM) or random access memory (CDRAM), or any other tangible optical, electrical, magnetic, or other storage device; or storage found on transmission media such as those supporting the Internet or an intranet, including temporary cache memory.

Computer program code for carrying out operations of the example embodiments may be written by conventional means using any computer language, including but not limited to, an interpreted or event driven language such as BASIC, Lisp, VBA, or VBScript, or a GUI embodiment such as visual basic, a compiled programming language such as FORTRAN, COBOL, or Pascal, an object oriented, scripted or unscripted programming language such as Java, JavaScript, Perl, Smalltalk, C++, Object Pascal, or the like, artificial intelligence languages such as Prolog, a real-time embedded language such as Ada, or even more direct or simplified programming using ladder logic, an Assembler language, or directly programming using an appropriate machine language.

The example computer program software for implementing the features described above comprises computer program instructions that are executed by providing the instructions to an executing device or component, which can include a processor of a general purpose computer, a special purpose computer or controller, or other programmable data processing apparatus or component, such that the instructions of the computer program, when executed, create means for implementing the functions/acts specified in the flowcharts and/or block diagram block or blocks shown some of the figures. Hence, the computer program instructions are used to cause a series of operations to be performed on the executing device or component, or other programmable apparatus to produce a computer implemented process such that the instructions which execute on the computer or other programmable apparatus then perform at least some the steps for implementing the functions/acts specified in this disclosure. These steps or acts may be combined with operator or human implemented steps or acts and steps or acts provided by other components or apparatuses in order to carry out any number of example embodiments of the invention.

The flowcharts and/or block diagrams illustrate example architecture, functionality, and operation of possible implementations of systems, methods and computer program products according to various example embodiments. In this regard, each block in the flowchart or block diagrams may represent a module, segment, or other portion of code that makes up the software, and thus which comprises one or more executable instructions for implementing the specified logical function(s). It should also be noted that, in some alternative implementations, the functions noted in the block may occur out of the order noted in the figures. For example, although the functions of two blocks shown in succession are typically accomplished in series, they may, in some circumstances where not logically inconsistent with the disclosure, be executed substantially concurrently, or the functions may sometimes be executed in the reverse order, depending upon the functionality involved. It will also be noted that each block of the block diagrams and/or flowchart illustration, and combinations of blocks in the block diagrams and/or flowchart illustration, can be implemented by a number of alternative solutions, including the use of special purpose hardware-based systems which perform the specified functions or acts, or combinations of special purpose hardware and computer instructions.

Many other example embodiments can be provided through various combinations of the above described features. Although the embodiments described hereinabove use specific examples and alternatives, it will be understood by those skilled in the art that various additional alternatives may be used and equivalents may be substituted for elements and/or steps described herein, without necessarily deviating from the intended scope of the application. Modifications may be necessary to adapt the embodiments to a particular situation or to particular needs without departing from the intended scope of the application. It is intended that the application not be limited to the particular example implementations and example embodiments described herein, but that the claims be given their broadest reasonable interpretation to cover all novel and non-obvious embodiments, literal or equivalent, disclosed or not, covered thereby.

What is claimed is:

1. A method for using a computer system including a server system and a computerized terminal for verifying provider services provided by a provider to a client in the client's home, said computerized terminal configured with a computer for executing software instructions stored in memory to perform said method comprising the steps of:
providing a client computerized terminal that remains in the client's home and that is configured to verify it is located in the client's home;
executing software instructions on the computerized terminal to provide a first user interface on the client computerized terminal adapted for accepting time information from the provider providing health services to the client at the client's home;
providing the computerized terminal with hardware comprising at least one interface configured to capture one or more physical features in a region of the computerized terminal by collecting data about said one or more physical features including data that physically identifies the client and data that physically identifies location of the computerized terminal at the client's home, wherein said hardware includes a GPS device, a biometric sensor, and/or a camera;
executing software instructions on the computerized terminal to provide a second user interface on the computerized terminal for displaying provider time worked based on the provider entered time information, aid second user interface configured for accepting information indicating client confirmation that the health services were received and that the client time worked is accurate;

the computerized terminal executing software instructions to generate validation information that uniquely identifies the client from the data that physically identifies the client from at least one of the one or more physical features;

the computerized terminal executing software instructions to generate verification information from the data that physically identifies location of the computerized terminal at the client's home from at least one of the one or more physical features, said verification information configured for verifying that the computerized terminal is located in the client's home during the steps of accepting the time information and capturing the validation information;

the computerized terminal executing software instructions to send the time information, the validation information, and the verification information to a remotely located server system connected to the computerized terminal via a communication network;

the remotely located server system having a computer for executing instructions stored by said server system to perform the step of using said verification information for verifying that the time information accepted from the provider was entered with the computerized terminal at the client's home;

the remotely located server system having the computer execute additional instructions stored by said server system to perform the step of using said validation information for confirming that the client received the health services; and subsequent to a successful verifying and confirming, using the computer of the remotely located server system remotely connected to said terminal via a communication network to execute additional instructions stored by said server system to perform the step of automatically generating and formatting an electronic bill configured for sending to a provider.

2. The method of claim 1, wherein the validation information is derived from physical features including one or more photographs taken by the terminal in the client's home.

3. The method of claim 2, wherein the one or more photographs are taken of one or more objects or rooms in the client's home.

4. The method of claim 1, wherein the verification information is derived from physical features including features indicating the location of the client's home.

5. The method of claim 1, wherein the computer server performs the verifying step.

6. The method of claim 1, wherein said bill is used for determining a paycheck amount for the provider.

7. The method of claim 1, further comprising the step of regularly synchronizing the computerized terminal with the computer server, wherein if said step of synchronizing fails, triggering a process for trouble checking.

8. The method of claim 7, wherein said regularly synchronizing is done every day at night.

9. The method of claim 1, further comprising the step of performing a client enrollment process prior to using the computerized terminal for accepting time information related to services provided to the client, wherein said enrollment process includes using information about the client that is provided by an external agency database that communications with the computer server via a network connection.

10. The method of claim 9, wherein said external agency database is a database provided for use by an insurance company.

11. The method of claim 9, wherein said external agency database is a database provided for use by a government agency.

12. The method of claim 9, wherein said client enrollment process includes the steps of the computer server electronically filling out one or more government forms and the computer server electronically transmitting said one or more government forms to a government agency.

13. The method of claim 1, further comprising the step of enrolling the provider using the computerized terminal located at the client's home, wherein said enrolling includes engaging the services of the provider for providing the health services to the client.

14. The method of claim 1, further comprising the step of the remotely located computer system warning the provider about a risk of exceeding a predetermined services threshold.

15. The method of claim 1, further providing a task interface screen on the user terminal configured to record which and at what time tasks of the health services occurred.

16. The method of claim 1, further comprising the step of providing a new task interface on the client computer configured to accept information about a new health services task that the provider provides to the client that was not originally a task assigned to the provider wherein subsequent to accepting the information about the new health services task, an indication that the task was added is provided for display by the client computerized terminal.

17. The method of claim 1, wherein at least one of the one or more physical features includes a radio signal detected in the client's home that indicates a location of the computerized terminal in the client's home.

18. The method of claim 1, wherein the interface configured to capture one or more physical features in a region of the computerized terminal is a biometric interface and wherein at least one of the one or more physical features includes a biometric feature of the client.

19. A method for using a computer system including a server system and a computerized terminal for verifying provider services provided by a provider to a client in the client's home, said method comprising the steps of:

storing client information in a centralized database in the server system;

executing software instructions on the computerized terminal to provide a client computerized terminal located in the client's home and that is configured to verify it is located in the client's home;

executing software instructions on the computerized terminal to connect the computerized terminal to the centralized database via a communication network for updating the computerized terminal for the client utilizing the client information stored in the centralized database;

the computerized terminal executing software instructions to perform the step of providing an enrollment interface on the computerized terminal for enrolling the provider using the computerized terminal, wherein said enrolling step includes an engagement step of the client using the enrollment interface for engaging the services of the provider for providing the health services to the client in the client's home, said engagement step including the step of using the enrollment interface for collecting additional information from the client regarding the health services to be performed with said additional information being entered into said computerized terminal using the enrollment interface for electronically capturing and storing said additional information in said centralized database;

using the client computerized terminal executing additional software instructions to perform the step of generating a user interface for accepting affirmation/refusal from the client using the enrollment interface for verifying that the client engaged the services of the provider for providing the health services;

providing the computerized terminal with hardware comprising at least one interface configured to capture one or more physical features in a region of the computerized terminal, wherein said hardware includes a GPS device, a biometric sensor, and/or a camera;

executing software instructions on the computerized terminal to capture data about one or more physical features in a region of the computerized terminal that physically identifies location of the computerized terminal at the client's home using the interface of the hardware of the computerized terminal;

the computerized terminal executing software instructions to generate verification information indicating a location of the computerized terminal using the data about the one or more physical features;

the computerized terminal executing software instructions to verify its location in the client's home during the step of enrolling the client using the verification information;

the computerized terminal executing software instructions to send information to update the centralized database via the communication network to capture the client enrollment affirmation/refusal;

using the computerized terminal executing additional software instructions to perform the step of capturing medical services information when the provider is providing the health services to the client for storing in the centralized database;

using the computerized terminal executing additional software instructions to perform the step of receiving validation information input from the client for verifying that the health services were provided to the client, said validation including using the verification information that verifies that the client entered the validation information while the client computerized terminal is located in the client's home; and subsequent to a successful verifying, using the computer of the remotely located server system remotely connected to said terminal via a communication network to execute additional instructions stored by said server system to perform the step of automatically generating and formatting an electronic bill configured for sending to a provider.

20. The method of claim 19, wherein the step of using the computerized terminal when the provider is providing the health services to the client includes the step of providing a time entry interface on the computerized terminal adapted for accepting time information from the provider providing health services to the client at the client's home.

21. The method of claim 20, further comprising the steps of:

the computerized terminal collecting the validation information for also verifying that the time information accepted from the provider was entered with the terminal located at the client's home;

using said validation information for verifying that the time information accepted from the provider was entered with the terminal at the client's home; and using said validation information for verifying that the time information accepted from the provider was entered with the terminal at the client's home.

22. The method of claim 21, further comprising the step of, subsequent to a successful verifying, using the computer server remotely connected to said terminal via the communication network for formatting an electronic bill according to a predetermined format acceptable to a payment agency separate from the provider.

23. The method of claim 19, further comprising the step of the computerized terminal collecting verification information for use in verifying that the enrollment step was accomplished with the terminal located at the client's home.

24. The method of claim 19, wherein said computerized terminal regularly synchronizes the client computerized terminal connected over a communication network with a remotely located computer server configured with software instructions for verifying and storing information about the provider provision of the health services to the client, wherein, if said step of synchronizing fails, a process for trouble checking is implemented.

25. The method of claim 24, wherein the step of using the computerized terminal for supporting providing the health services to the client includes the step of providing a time entry interface on the computerized terminal adapted for accepting time information from the provider providing health services to the client at the client's home.

26. The method of claim 25, further comprising the steps of:

the computerized terminal using at least one of said one or more physical features for generating verification information for verifying that the time information accepted from the provider was entered with the terminal located at the client's home;

sending said verification information to the remotely located server system via the communication network;

said server system using said verification information for verifying that the time information accepted from the provider was entered with the terminal at the client's home; and said server system using said validation information for verifying that the client received the health services.

27. The method of claim 26, further comprising the step of, subsequent to a successful verifying, using a computer server remotely connected to said terminal via a communication network for formatting an electronic bill according to a predetermined format acceptable to a payment agency separate from the provider.

28. The method of claim 24, further comprising the steps of:

providing an enrollment interface for enrolling the provider using the computerized terminal, wherein said enrolling step includes the step of the client engaging the services of the provider for providing the health services to the client in the client's home, said engaging step including the step of collecting information from the client regarding the health services to be performed; and using the computerized terminal for verifying that the client engaged the services of the provider for providing the health services.

29. The method of claim 28, further comprising the step of the computerized terminal using at least one of said one or more physical features for generating verification information for use in verifying that the enrollment step was accomplished with the terminal located at the client's home.

30. The method of claim 24, wherein the step of for supporting providing the health services to the client includes the step of providing a time entry interface on the computerized terminal adapted for accepting time information from the provider providing health services to the client at the client's home.

31. The method of claim 30, further comprising the steps of:
- the computerized terminal using data about at least one of said one or more physical features for generating verification information for verifying that the time information accepted from the provider was entered with the terminal located at the client's home;
- sending said verification information to the remotely located server system via the communication network;
- said server system using said verification information for verifying that the time information accepted from the provider was entered with the terminal at the client's home; and
- said server system using said validation information for verifying that the client received the health services.

32. A method for using a computer system including a server system and a computerized terminal for verifying provider services provided by a provider to a client in the client's home, said computerized terminal configured with a computer for executing software instructions stored in memory to perform said method comprising the steps of:
- providing a first user interface on the computerized terminal adapted for accepting time information from the provider providing health services to the client at the client's home;
- providing the computerized terminal with biometric hardware including an interface configured to capture biometric data about a biometric feature of the client;
- the computerized terminal executing software instructions to convert the biometric data into validation information uniquely identifying the client, wherein said validation information also includes information indicating client confirmation that the health services were received;
- the computerized terminal having additional hardware including an interface configured to capture location data about one or more physical features in a region of the computerized terminal;
- the computerized terminal executing software instructions to generate verification information from the location data, said verification information used for verifying that the time information accepted from the provider was entered with the terminal located at the client's home;
- the computerized terminal executing software instructions to send the time information, the validation information, and the verification information to a remotely located server system connected to the computerized terminal via a communication network;
- the remotely located server system having a computer for executing instructions stored by said server system to perform the step of using said verification information for verifying that the time information accepted from the provider was entered with the terminal at the client's home;
- the remotely located server system having the computer for execute additional instructions stored by said server system to perform the step of using said validation information for confirming that the client received the health services; and
- subsequent to a successful verifying and confirming, using the computer of the remotely located server system remotely connected to said terminal via a communication network to execute additional instructions stored by said server system to perform the step of automatically generating and formatting an electronic bill configured for sending to a provider.

* * * * *